United States Patent
Cuzzato

(10) Patent No.: US 6,307,114 B1
(45) Date of Patent: *Oct. 23, 2001

(54) PROCESS FOR PREPARING 1,1,1-TRIFLUORO-2-CHLOROETHANE

(75) Inventor: Paolo Cuzzato, Treviso (IT)

(73) Assignee: Ausimont S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/885,624

(22) Filed: Jun. 30, 1997

Related U.S. Application Data

(63) Continuation of application No. 08/540,404, filed on Oct. 6, 1995, now abandoned, which is a continuation of application No. 08/342,798, filed on Nov. 21, 1994, now abandoned, which is a continuation of application No. 08/104,720, filed on Aug. 11, 1993, now abandoned.

(30) Foreign Application Priority Data

Aug. 14, 1992 (IT) ............................................... MI92A1991

(51) Int. Cl.$^7$ ................................................. C07C 17/08
(52) U.S. Cl. ........................................... 570/169; 570/168
(58) Field of Search .................................... 570/168, 169

(56) References Cited

U.S. PATENT DOCUMENTS

| | | |
|---|---|---|
| 2,637,747 | 5/1953 | McBee . |
| 2,885,427 | 5/1959 | Ruh et al. . |
| 3,752,850 | 8/1973 | Scherer et al. . |
| 3,755,477 | 8/1973 | Firth et al. . |
| 4,967,023 * | 10/1990 | Carmello et al. ............ 570/188 |
| 5,185,482 * | 2/1993 | Manzer .................... 570/165 |
| 5,334,786 * | 8/1994 | Koyama et al. ............ 570/168 |

FOREIGN PATENT DOCUMENTS

| | | |
|---|---|---|
| 1104496 | 4/1959 | (DE) . |
| 1246703 * | 8/1967 | (DE) .................... 570/169 |
| 408005 | 1/1991 | (EP) . |
| 446869 | 9/1991 | (EP) . |
| 449614 | 10/1991 | (EP) . |
| A-449614 | 10/1991 | (EP) . |
| 1383927 | 11/1963 | (FR) . |
| 1000485 | 2/1962 | (GB) . |
| PCT/EP 90/08755 | 8/1990 | (WO) . |

OTHER PUBLICATIONS

European Search Report for EP–A–93 11 2630.

* cited by examiner

*Primary Examiner*—Alan Siegel
(74) *Attorney, Agent, or Firm*—Bryan Cave LLP

(57) ABSTRACT

In the preparation of 1,1,1-trifluoro-2-chloroethane (HCFC 133$a$) by means of hydrofluorination in the gas phase of trichloroethylene (TCE) in the presence of a carried catalyst based on $Cr_2O_3$ it is possible to prolong the catalyst life by feeding to the hydrofluorination reactor, along with trichloroethylene, little amounts (7–25 mols % calculated on the mixture with trichloroethylene) of 133$a$.

2 Claims, No Drawings

PROCESS FOR PREPARING 1,1,1-TRIFLUORO-2-CHLOROETHANE

This is a continuation of U.S. application Ser. No. 08/540,404, filed Oct. 6, 1995 now abandoned, which was a continuation of U.S. application Ser. No. 08/342,798, filed Nov. 21, 1994, now abandoned, which was a continuation of U.S. application Se. No. 08/104,720, filed Aug. 11, 1993, now abandoned.

The present invention relates to an improvement in the preparation of 1,1,1-trifluoro-2-chloroethane (hereinafter referred to as HCFC 133a), carried out by hydrofluorination of trichloroethylene (TCE) in the gas phase, in the presence of chrome oxide and/or chrome oxyfluorides or fluorides as catalysts.

Preparations of HCFC 133a according to such method are broadly described in the art; in this connection, reference should be made to patents: U.S. Pat. Nos. 3,752,850; 2,637,747; 2,885,427; 3,755,477; GB 1,000,485; DE 1,104,496.

A serious drawback affecting the preparation of HCFC 133a according to the abovesaid method is represented by the decay of the catalyst activity during the reaction.

So, for examples, if a mixture of trichloroethylene and anhydrous HF in a 1/6 molar ratio is conveyed onto a catalyst based on chrome oxide and/or chrome oxyfluoride or fluoride carried on fluorinated alumina, with a contact time of 5 seconds, the starting conversion of trichloroethylene is very high (typically of 90–95%), which, however, gradually decreases at a rate which is depending on temperature. For example, at 300° C. the conversion begins to decrease after 25 hours and sinks to 80%, within 90 hours, while at 350° C. the conversion sinks to 70–75% in 50 hours.

To overcome this drawback it was suggested to add air or oxygen to the reagent mixture.

Such method, however, is affected by the serious drawback of promoting dismutation reactions of the reaction intermediate products, giving rise to great amounts of undesired products. For example, maintaining the abovesaid conditions, with the exception of the addition of air in a $O_2$/trichloroethylene molar ratio equal to 1/6, about 6% by weight of dismutation products form, while in the absence of air such products form only in amounts of 0.5–0.6% by weight.

Furthermore, if it is operated in the presence of oxygen, the amount of 1,1-difluoro-2-chloroethylene (undesired product owing to its toxicity) rises from 0.02–0.03% to 0.250–0.30% by weight.

Lastly, operating in the presence of oxygen, the trichloroethylene conversion is slightly lower (88–90%) as compared with the cases when it is operated in the absence of oxygen.

It has now surprisingly been found by the Applicant that it is possible to maintain for a long period of time the catalyst activity and selectivity by adding to the reaction mixture, composed of trichloroethylene and of hydrofluoric acid, little amounts of HCFC 133a, what, in terms of plant engineering, is equivalent to recycle to the reactor a little part of the reaction product, optionally comprising the unreacted trichloroethylene and hydrofluoric acid.

A further advantage of this operating method resides in the fact that the formation of by-products decreases instead of increasing, as conversely happens when it is operated in the presence of oxygen.

The amount of HCFC 133a to be added to the reagent mixture sent to the reactor shall be at least of 7 mols %, and preferably of at least 10 mols %, referred to the mixture with trichloroethylene.

Generally, HCFC 133a amounts ranging from 7 to 25 mols % and preferably from 10 to 20 mols %, calculated on its mixture with trichloroethylene, can be considered as suitable for the purposes of the invention.

The reaction temperature suitably ranges from 250° to 330° C., preferably from 280° to 300° C.

From European patent application 449,614 it is known a process for preparing 1,1,1-trifluoro-2-fluoroethane by hydrofluorination of trichloroethylene, which process comprises a step of preparing 1,1,1-trifluoro-2-chloroethane (step D) via hydrofluorination of mixtures of said 1,1,1-trifluoro-2-chloroethane with trichloroethylene.

In such step, however, the amount of 1,1,1-trifluoro-2-chloroethane in the mixture is always by far prevailing on the amount of trichloroethylene (which, according to the examples, is of about 15 mols %), wherefore the conditions of the present invention do not exist in such process, nor the advantages are inferable therefrom.

Thus, it is an object of the present invention to provide a process for preparing HCFC 133a by hydrofluorination of trichloroethylene with hydrofluoric acid in the gas phase, in the presence of catalysts composed of chrome oxide and/or chrome oxyfluorides or fluorides and carried on at least partially fluorinated alumina, carried out under the above-described conditions.

The catalyst can be prepared according to any method of the art.

Preferably it is prepared by impregnating an alumina carrier, which had been at least partially previously fluorinated, with an aqueous solution of a trivalent chrome salt, by drying the whole and activating with air or nitrogen, either or not in the presence of water and/or crystallization water which can act as an oxidizer, at temperatures ranging from 200° to 600° C., but preferably from 350° to 500° 1 C., in order to convert chrome into $Cr_2O_3$.

Preferably, but not necessarily, the catalyst is then treated, prior to the use, with gaseous HF, at a temperature from 200° to 450° C., optionally in the same reactor to be used for the reaction of trichloroethylene and HF.

By at least partially fluorinated alumina is meant herein the alumina comprising at least 50%, but preferably at least 90% by weight of $AlF_3$.

Such a fluorinated alumina is preparable by hydrofluorination of alumina according to what is described in FR patent No. 1,383,927.

The chrome amount on the carrier preferably ranges from 1 to 15% by weight calculated on the total weight of the catalyst.

The carrier can be in the form of a powder having particle size from 20 to 200 microns, or in the form of pellets.

The at least partially fluorinated alumina used as a carrier comprises $AlF_3$ mainly in the gamma and/or beta forms; however also the delta form can be present up to amounts of 30% by weight.

Also $AlF_3$ in the alpha form can be present, however in little amounts.

Another method of preparing the catalyst comprises soaking the alumina with an aqueous solution of a chrome salt, drying and then, optionally, subjecting the resulting product to fluorination with HF till obtaining a fluorination of the alumina for at least 50% and preferably for at least 90%.

A further method comprises coprecipitating the aluminium and chrome hydroxides, drying them, subjecting them to calcination in order to convert them into mixed oxides and, lastly, treating them with HF till obtaining the desired alumina fluorination degree.

In the trichloroethylene hydrofluorination reaction it is preferably operated with HF/trichloroethylene molar ratios higher than 3/1. Generally, ratios between 5/1 and 10/1 are utilized.

The pressure is not critical; generally it is operated at atmospheric pressure.

The following examples are given to illustrate the present invention, without being however a limitation thereof.

EXAMPLE 1

A catalyst was prepared by impregnating fluorinated alumina (containing 95% by weight of $AlF_3$) with an aqueous solution of $CrCl_3.6H_2O$, by drying and activating then the catalyst by means of treatment with $N_2$ at 400° C. for 8–10 hours.

390 cc of such catalyst were introduced into a reactor consisting of an INCONEL® tube having a diameter of 50 mm, electrically heated and equipped with a sintered INCONEL fritted bottom.

Then, at a temperature of 300° C. there were fed 0.686 mols/h of trichloroethylene, 0.171 mols/h of HCFC 133a and 5.14 mols/h of anhydrous hydrofluoric acid, thereby obtaining a contact time of 5 seconds (measured as the ratio of the reagent volume at the reaction temperature to the volume of the catalytic bed at rest), a HF/organic products ratio of 6/1 and a HCFC 133a/trichloroethylene ratio of 1/4.

The gases leaving the reactor were scrubbed in water to eliminate their acidity, were dried and analyzed via GLC.

The following analysis, expressed in mols per cent, carried out after 48.5 hours, is representative: A134a=1.9; A133a=92.3; TCE=4.8; A1121=0.9; A143a=0.1; besides negligible amounts of other products.

The trichloroethylene conversion was of 93.8% and after more than 70 hours of run under these conditions it was still the same, without any sign of decay of the catalyst performances, as well as the selectivity for 133a.

EXAMPLE 2

It was operated in the same reactor and under the same test conditions of example 1, varying only the 133a/trichloroethylene molar ratio, which in this case was equal to 1/9.

The catalytic bed volume was slightly smaller (350 cc) and therefore the flowrates were reduced in order to keep the contact time constant. The other operative conditions were as follows: HF=3.94 mols/h; HCFC 133a =0.066; TCE= 0.59.

Operating as in example 1, rather constant results in the course of time were obtained. The following analysis of the effluents, carried out after 63 hours, is representative: A134a=1.5; A133a=90.7; TCE=6.5; A1121=0.9; A1122= 0.1; other by-products=0.2.

The trichloroethylene conversion was equal to 92.6% and during a run of more than 85 hours it remained at 90–95% without signs of catalyst exhaustion.

EXAMPLE 3

Comparative

It was operated in the same reactor and under the same test conditions of the preceding examples. 390 g, equal to 300 cc, of a previously activated catalyst, as is described in example 1, were charged, and at 300° C. there were fed 4.10 mols/h of anhydrous hydrofluoric acid and 0.68 mols/h of trichloroethylene, so obtaining a contact time of 5 seconds and a HF/TCE ratio equal to 6.

The starting conversion was of 95–96% and gradually decreased to about 70% during a 68-hour run.

The reaction products were substantially the same as in the preceding examples as regards both nature and distribution, the conversion being equal; the following per cent analysis, carried out after a 20-hour run, is representative of obtained products: A134a=1.3; A133a=92.4; TCE= 4.4; A1121=1.1; A1122=negligible; other by-products=0.6.

EXAMPLE 4

Use of Oxygen 390 g, equal to 300 cc, of catalyst already activated according to example 1 were charged into the reactor of the preceding examples. At 350° C. there were fed 0.21 mols/h of trichloroethylene, 1.73 mols/h of anhydrous HF and 4.15 1/h of air (equal to 0.035 mols of $O_2$) so obtaining a contact time of 10 seconds, a HF/trichloroethylene molar ratio of about 8/1 and a $O_2$/trichloroethylene molar ratio equal to 1/6.

Operating as in the preceding examples there were obtained the results represented by the following mols per cent analysis of the products flowing from the reactor: A134a=2.3; A133a=81.3; TCE=8.9; intermediates =2.0; A1122=0.4; other by-products=5.0.

The trichloroethylene conversion was equal to 91.1 % and the by-products amounted to about 5.5% of the converted product.

What is claimed is:

1. A process for the preparation of 1,1,1-trifluoro-2-chloroethane by reacting, in the gas phase, a mixture consisting of 1,1,1-trifluoro-2-chloroethane and trichloroethylene in a molar ratio from 7:93 to 25:75 with hydrogen fluoride in the presence of a catalyst consisting of chromium trioxide carried on aluminum trifluoride at a temperature from 280 degrees celsius to 300 degrees celsius.

2. The process of claim 1, wherein the reaction is carried out in the presence an amount of 1,1,1-trifluoro-2-chloroethane such that the molar ratio of 1,1,1-trifluoro-2-chloroethane to trichloroethylene is from 10:90 to 20:80.

* * * * *

UNITED STATES PATENT AND TRADEMARK OFFICE
CERTIFICATE OF CORRECTION

PATENT NO.   : 6,307,114 B1
DATED        : October 23, 2001
INVENTOR(S)  : Paolo Cuzzato Page 1 of 1

It is certified that error appears in the above-identified patent and that said Letters Patent is hereby corrected as shown below:

Column 4,
Line 53, after "presence" please insert -- of --.

Signed and Sealed this

Seventh Day of May, 2002

Attest:

Attesting Officer

JAMES E. ROGAN
*Director of the United States Patent and Trademark Office*